(12) United States Patent
Stoller et al.

(10) Patent No.: US 11,986,381 B2
(45) Date of Patent: May 21, 2024

(54) SIDE-SPECIFIC ORTHOPAEDIC SURGICAL INSTRUMENT SYSTEMS AND ASSOCIATED METHODS OF USE

(71) Applicant: DEPUY IRELAND UNLIMITED COMPANY, Ringaskiddy (IE)

(72) Inventors: Dennis A. Stoller, Fort Wayne, IN (US); Stephanie M. Wainscott, Fort Wayne, IN (US); Jonathan C. Lee, Mishawaka, IN (US); Rebecca L. Chaney, Warsaw, IN (US)

(73) Assignee: DEPUY IRELAND UNLIMITED COMPANY (IE)

( * ) Notice: Subject to any disclaimer, the term of this patent is extended or adjusted under 35 U.S.C. 154(b) by 0 days.

(21) Appl. No.: 18/209,019

(22) Filed: Jun. 13, 2023

(65) Prior Publication Data
US 2023/0320833 A1    Oct. 12, 2023

Related U.S. Application Data

(60) Division of application No. 17/193,471, filed on Mar. 5, 2021, now Pat. No. 11,672,638, which is a
(Continued)

(51) Int. Cl.
*A61B 50/33* (2016.01)
*A61B 17/15* (2006.01)
(Continued)

(52) U.S. Cl.
CPC .......... *A61F 2/0095* (2013.01); *A61B 17/155* (2013.01); *A61B 17/1764* (2013.01);
(Continued)

(58) Field of Classification Search
CPC ....... A61B 50/33; A61B 50/22; A61F 2/0095; A61F 2002/3069; A61F 2/4684
(Continued)

(56) References Cited

U.S. PATENT DOCUMENTS

| 5,318,543 A | 6/1994 | Ross et al. |
| 5,597,384 A | 1/1997 | Walker et al. |

(Continued)

FOREIGN PATENT DOCUMENTS

| DE | 202007000934 U1 | 4/2007 |
| EP | 1393695 A1 | 3/2004 |

(Continued)

OTHER PUBLICATIONS

Zimmer, Inc., "Instrument Care, Cleaning and Sterilization Instruction"; www.zimmer.com; Feb. 6, 2004; Retrieved Jan. 6, 2011 from the Internet URL: http://www.zimmer.co.nz/web/enUS/pdf/Surgical.sub.-Cleaning.sub.-I- nstructions.sub.-Final.pdf; COPYRGT. 1987, 1988, 2002 Zimmer Inc.; USA.

(Continued)

*Primary Examiner* — Steven A. Reynolds
(74) *Attorney, Agent, or Firm* — Barnes & Thornburg LLP

(57) ABSTRACT

A surgical instrument system includes a pair of side-specific orthopaedic surgical instrument assemblies. The right-limb side-specific instrument assembly is kitted so as to be devoid of left-limb side-specific instruments and vice versa.

7 Claims, 2 Drawing Sheets

Related U.S. Application Data continuation of application No. 15/709,100, filed on Sep. 19, 2017, now Pat. No. 10,940,022.

(51) Int. Cl.

| | | |
|---|---|---|
| *A61B 17/17* | (2006.01) | |
| *A61B 50/20* | (2016.01) | |
| *A61F 2/00* | (2006.01) | |
| *A61B 90/00* | (2016.01) | |
| *A61F 2/30* | (2006.01) | |
| *A61F 2/38* | (2006.01) | |
| *A61F 2/46* | (2006.01) | |

(52) U.S. Cl.
CPC .............. *A61B 50/20* (2016.02); *A61B 50/33* (2016.02); *A61B 2090/0813* (2016.02); *A61F 2002/30616* (2013.01); *A61F 2002/3069* (2013.01); *A61F 2002/30708* (2013.01); *A61F 2/3859* (2013.01); *A61F 2/3886* (2013.01); *A61F 2/4684* (2013.01)

(58) Field of Classification Search
USPC .................................................. 206/370, 363
See application file for complete search history.

(56) References Cited

U.S. PATENT DOCUMENTS

| | | | |
|---|---|---|---|
| 5,776,201 A * | 7/1998 | Colleran | ............... A61F 2/4684 606/88 |
| 5,779,053 A | 7/1998 | Partika et al. | |
| 6,158,437 A | 12/2000 | Vagley | |
| 6,783,004 B1 | 8/2004 | Rinner | |
| 6,793,078 B2 | 9/2004 | Roshdy | |
| 8,701,890 B2 | 4/2014 | Bertazzoni et al. | |
| 9,980,828 B2 * | 5/2018 | Meulink | ................... A61F 2/46 |
| 10,940,022 B2 * | 3/2021 | Stoller | ................ A61B 17/1764 |
| 11,672,638 B2 * | 6/2023 | Stoller | ................. A61F 2/0095 206/370 |
| 2003/0121821 A1 | 7/2003 | Roshdy | |
| 2005/0033430 A1 | 2/2005 | Powers et al. | |
| 2006/0124486 A1 | 6/2006 | Faust et al. | |
| 2006/0217815 A1 | 9/2006 | Gibbs et al. | |
| 2006/0223035 A1 | 10/2006 | Fischer | |
| 2007/0034538 A1 | 2/2007 | Landis | |
| 2008/0021567 A1 | 1/2008 | Meulink et al. | |
| 2009/0194446 A1 | 8/2009 | Miller et al. | |
| 2010/0065456 A1 | 3/2010 | Junk et al. | |
| 2011/0071572 A1 * | 3/2011 | Sixto | ................. A61B 17/8014 606/286 |
| 2011/0186456 A1 * | 8/2011 | Bertazzoni | ................ A61F 2/38 606/89 |
| 2014/0224704 A1 * | 8/2014 | Bertazzoni | ................ A61F 2/38 206/570 |
| 2017/0333212 A1 | 11/2017 | Wolfson et al. | |

FOREIGN PATENT DOCUMENTS

| | | |
|---|---|---|
| FR | 2904527 A1 | 2/2008 |
| JP | H07-178116 A | 7/1995 |
| RU | 2360637 C1 | 7/2009 |
| WO | 0152762 A1 | 7/2001 |
| WO | 2004006811 A2 | 1/2004 |
| WO | 2005016183 A1 | 2/2005 |

OTHER PUBLICATIONS

Extended European Search Report for Application No. EP 18 19 4429 dated Feb. 4, 2019, 9 pages.
Japanese Office Action for Patent Application 2018-173344, dated Jul. 12, 2022, 3 pages.

* cited by examiner

SIDE-SPECIFIC ORTHOPAEDIC SURGICAL INSTRUMENT SYSTEMS AND ASSOCIATED METHODS OF USE

This is a divisional application that claims priority to U.S. patent application Ser. No. 17/193,471, now U.S. Pat. No. 11,672,638, which was filed on Mar. 5, 2021, which is a continuation application that claims priority to U.S. patent application Ser. No. 15/709,100, now U.S. Pat. No. 10,940,022, which was filed on Sep. 19, 2017, the entirety of each of the above-identified applications is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a revision knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During either a primary or revision knee surgery, the orthopaedic surgeon typically uses a variety of different orthopaedic surgical instruments such as, for example, cutting blocks, reamers, drill guides, prosthetic trials, and other surgical instruments to prepare the patient's bones to receive the knee prosthesis. Such surgical instruments may be constructed of either metal or polymer materials and are generally designed to be reusable. After use, reusable surgical instruments are kitted into trays, sterilized, and returned to the operating room for use in a subsequent procedure. The kits are assembled by size irrespective of whether the upcoming procedure is a right-limb or left-limb procedure. This is done so that similar instruments are kitted together. For example, a typical size-based kit for a revision knee procedure includes both the left-limb side-specific and right-limb side-specific femoral trial components in sizes 3, 4, and 5 with a different kit including both side-specific femoral trial components (i.e., both left and right) in sizes 6, 7, and 8. However, revision knee surgery is rarely bilateral. As a result, half the trial components—i.e., the components specific to the limb not being operated on—go unused and, as a result, unnecessarily consume resources such as table space, cleaning, and subsequent sterilization.

SUMMARY

According to one aspect of the disclosure, a surgical instrument system includes a plurality of orthopaedic surgical instruments. The orthopaedic surgical instruments include a plurality of right-limb side-specific orthopaedic trial components. Each of the plurality of right-limb side-specific orthopaedic trial components has a size that is different from the size of at least some of the other of the plurality of right-limb side-specific orthopaedic trial components. The orthopaedic surgical instruments also include a plurality of left-limb side-specific orthopaedic trial components, with each of the plurality of left-limb side-specific orthopaedic trial components having a size that is different from the size of at least some of the other of the plurality of left-limb side-specific orthopaedic trial components. The surgical instrument system also includes a first instrument sterilization tray that has a plurality of instrument retainers configured to retain the orthopaedic surgical instruments during sterilization and transport thereof. The first instrument sterilization tray is devoid of any of the plurality of left-limb side-specific orthopaedic trial components when each of the plurality of instrument retainers has one of the plurality of orthopaedic surgical instruments retained thereto. The orthopaedic surgical system also includes a second instrument sterilization tray having a plurality of instrument retainers configured to retain the orthopaedic surgical instruments during sterilization and transport thereof. The second instrument sterilization tray is devoid of any of the plurality of right-limb side-specific orthopaedic trial components when each of the plurality of instrument retainers has one of the plurality of orthopaedic surgical instruments retained thereto.

The plurality of right-limb side-specific orthopaedic trial components may include a plurality of right-limb side-specific femoral trial components, and the plurality of left-limb side-specific orthopaedic trial components may include a plurality of left-limb side-specific femoral trial components. In an embodiment, the first instrument sterilization tray is devoid of any of the plurality of left-limb side-specific femoral trial components when each of the plurality of instrument retainers has one of the plurality of orthopaedic surgical instruments retained thereto, with the second instrument sterilization tray being devoid of any of the plurality of right-limb side-specific femoral trial components when each of the plurality of instrument retainers has one of the plurality of orthopaedic surgical instruments retained thereto.

In an embodiment, each of the plurality of right-limb side-specific femoral trial components has a size that is different from the size of each of the other of the plurality of right-limb side-specific femoral trial components. Similarly, each of the plurality of left-limb side-specific femoral trial components may have a size that is different from the size of each of the other of the plurality of left-limb side-specific femoral trial components.

The plurality of right-limb side-specific femoral trial components may be embodied as a plurality of right-limb side-specific femoral cut-through trial components, and the plurality of left-limb side-specific femoral trial components may be embodied as a plurality of left-limb side-specific femoral cut-through trial components.

In an embodiment, the plurality of right-limb side-specific orthopaedic trial components includes a plurality of right-limb side-specific intramedullary connector components, and the plurality of left-limb side-specific orthopaedic trial components includes a plurality of left-limb side-specific intramedullary connector components. In such an embodiment, the first instrument sterilization tray is devoid of any of the plurality of left-limb side-specific intramedullary connector components when each of the plurality of instrument retainers has one of the plurality of orthopaedic surgical instruments retained thereto, and the second instrument sterilization tray is devoid of any of the plurality of right-limb side-specific intramedullary connector components when each of the plurality of instrument retainers has one of the plurality of orthopaedic surgical instruments retained thereto.

Illustratively, each of the plurality of right-limb side-specific intramedullary connector components may have a size that is different from the size of each of the other of the plurality of right-limb side-specific intramedullary connector components, and each of the plurality of left-limb side-specific intramedullary connector components may have a size that is different from the size of each of the other of the plurality of left-limb side-specific intramedullary connector components.

In one embodiment, the plurality of right-limb side-specific orthopaedic trial components includes a plurality of right-limb side-specific box trial components, and the plurality of left-limb side-specific orthopaedic trial components includes a plurality of left-limb side-specific box trial components. In such an embodiment, the first instrument sterilization tray is devoid of any of the plurality of left-limb side-specific box trial components when each of the plurality of instrument retainers has one of the plurality of orthopaedic surgical instruments retained thereto, and the second instrument sterilization tray is devoid of any of the plurality of right-limb side-specific box trial components when each of the plurality of instrument retainers has one of the plurality of orthopaedic surgical instruments retained thereto.

Illustratively, each of the plurality of right-limb side-specific box trial components may have a size that is different from the size of each of the other of the plurality of right-limb side-specific box trial components, and each of the plurality of left-limb side-specific box trial components may have a size that is different from the size of each of the other of the plurality of left-limb side-specific box trial components.

In another embodiment, the plurality of right-limb side-specific orthopaedic trial components includes a plurality of right-limb side-specific femoral reamer guide components, and the plurality of left-limb side-specific orthopaedic trial components includes a plurality of left-limb side-specific femoral reamer guide components. In such an embodiment, the first instrument sterilization tray is devoid of any of the plurality of left-limb side-specific femoral reamer guide components when each of the plurality of instrument retainers has one of the plurality of orthopaedic surgical instruments retained thereto, and the second instrument sterilization tray is devoid of any of the plurality of right-limb side-specific femoral reamer guide components when each of the plurality of instrument retainers has one of the plurality of orthopaedic surgical instruments retained thereto.

Illustratively, each of the plurality of right-limb side-specific femoral reamer guide components has a size that is different from the size of each of the other of the plurality of right-limb side-specific femoral reamer guide components, and each of the plurality of left-limb side-specific femoral reamer guide components has a size that is different from the size of each of the other of the plurality of left-limb side-specific femoral reamer guide components.

According to another aspect, a surgical instrument system has a plurality of orthopaedic surgical instruments including a plurality of right-limb side-specific femoral trial components in which each of the plurality of right-limb side-specific femoral trial components has a size that is different from the size of each of the other of the plurality of right-limb side-specific femoral trial components, and a plurality of left-limb side-specific femoral trial components in which each of the plurality of left-limb side-specific femoral trial components has a size that is different from the size of each of the other of the plurality of left-limb side-specific femoral trial components. The system also includes a first instrument sterilization tray having a plurality of instrument retainers configured to retain the orthopaedic surgical instruments during sterilization and transport thereof. The first instrument sterilization tray is devoid of any of the plurality of left-limb side-specific femoral trial components when each of the plurality of instrument retainers has one of the plurality of orthopaedic surgical instruments retained thereto. The system also includes a second instrument sterilization tray having a plurality of instrument retainers configured to retain the orthopaedic surgical instruments during sterilization and transport thereof. The second instrument sterilization tray is devoid of any of the plurality of right-limb side-specific femoral trial components when each of the plurality of instrument retainers has one of the plurality of orthopaedic surgical instruments retained thereto.

The plurality of right-limb side-specific femoral trial components may be embodied as a plurality of right-limb side-specific femoral cut-through trial components, and the plurality of left-limb side-specific femoral trial components may be embodied as a plurality of left-limb side-specific femoral cut-through trial components.

The plurality of orthopaedic surgical instruments may further include a plurality of right-limb side-specific intramedullary connector components, and a plurality of left-limb side-specific intramedullary connector components. In such an embodiment, the first instrument sterilization tray is devoid of any of the plurality of left-limb side-specific intramedullary connector components when each of the plurality of instrument retainers has one of the plurality of orthopaedic surgical instruments retained thereto, and the second instrument sterilization tray is devoid of any of the plurality of right-limb side-specific intramedullary connector components when each of the plurality of instrument retainers has one of the plurality of orthopaedic surgical instruments retained thereto.

Illustratively, each of the plurality of right-limb side-specific intramedullary connector components may have a size that is different from the size of each of the other of the plurality of right-limb side-specific intramedullary connector components, and each of the plurality of left-limb side-specific intramedullary connector components may have a size that is different from the size of each of the other of the plurality of left-limb side-specific intramedullary connector components.

In an embodiment, the plurality of orthopaedic surgical instruments further includes a plurality of right-limb side-specific box trial components, and a plurality of left-limb side-specific box trial components. In such an embodiment, the first instrument sterilization tray is devoid of any of the plurality of left-limb side-specific box trial components when each of the plurality of instrument retainers has one of the plurality of orthopaedic surgical instruments retained thereto, and the second instrument sterilization tray is devoid of any of the plurality of right-limb side-specific box trial components when each of the plurality of instrument retainers has one of the plurality of orthopaedic surgical instruments retained thereto.

Illustratively, each of the plurality of right-limb side-specific box trial components has a size that is different from the size of each of the other of the plurality of right-limb side-specific box trial components, and each of the plurality of left-limb side-specific box trial components has a size that is different from the size of each of the other of the plurality of left-limb side-specific box trial components.

The plurality of orthopaedic surgical instruments may further include a plurality of right-limb side-specific femoral reamer guide components, and a plurality of left-limb side-specific femoral reamer guide components. In such an embodiment, the first instrument sterilization tray is devoid of any of the plurality of left-limb side-specific femoral reamer guide components when each of the plurality of instrument retainers has one of the plurality of orthopaedic surgical instruments retained thereto, and the second instrument sterilization tray is devoid of any of the plurality of right-limb side-specific femoral reamer guide components when each of the plurality of instrument retainers has one of the plurality of orthopaedic surgical instruments retained thereto.

Illustratively, each of the plurality of right-limb side-specific femoral reamer guide components has a size that is different from the size of each of the other of the plurality of right-limb side-specific femoral reamer guide components, and each of the plurality of left-limb side-specific femoral reamer guide components has a size that is different from the size of each of the other of the plurality of left-limb side-specific femoral reamer guide components.

According to a further aspect, a method of using a surgical instrument system includes positioning a plurality of right-limb side-specific orthopaedic trial components in a first instrument sterilization tray and a plurality of left-limb side-specific orthopaedic trial components in a second instrument sterilization tray such that the first instrument sterilization tray is devoid of any of the plurality of left-limb side-specific orthopaedic trial components, and the second instrument sterilization tray is devoid of any of the plurality of right-limb side-specific orthopaedic trial components. The first instrument tray and the second instrument tray are then sterilized and at least one of the first instrument tray and the second instrument tray is utilized during performance of an orthopaedic surgical procedure.

In an embodiment, the first instrument tray is utilized during performance of an orthopaedic surgical procedure on a right limb of a patient.

The second instrument tray may be utilized during performance of an orthopaedic surgical procedure on a left limb of a patient.

A plurality of right-limb side-specific femoral trial components may be positioned in the first tray, and a plurality of left-limb side-specific femoral trial components may be positioned in the second tray.

In an embodiment, a plurality of right-limb side-specific intramedullary connector components is positioned in the first tray, and a plurality of left-limb side-specific intramedullary connector components is positioned in the second tray.

Illustratively, a plurality of right-limb side-specific box trial components is positioned in the first tray, and a plurality of left-limb side-specific box trial components is positioned in the second tray.

In an embodiment, a plurality of right-limb side-specific femoral reamer guide components is positioned in the first tray, and a plurality of left-limb side-specific femoral reamer guide components is positioned in the second tray.

BRIEF DESCRIPTION OF THE DRAWINGS

The detailed description particularly refers to the following figures, in which.

DETAILED DESCRIPTION OF THE DRAWINGS

Figure 1:
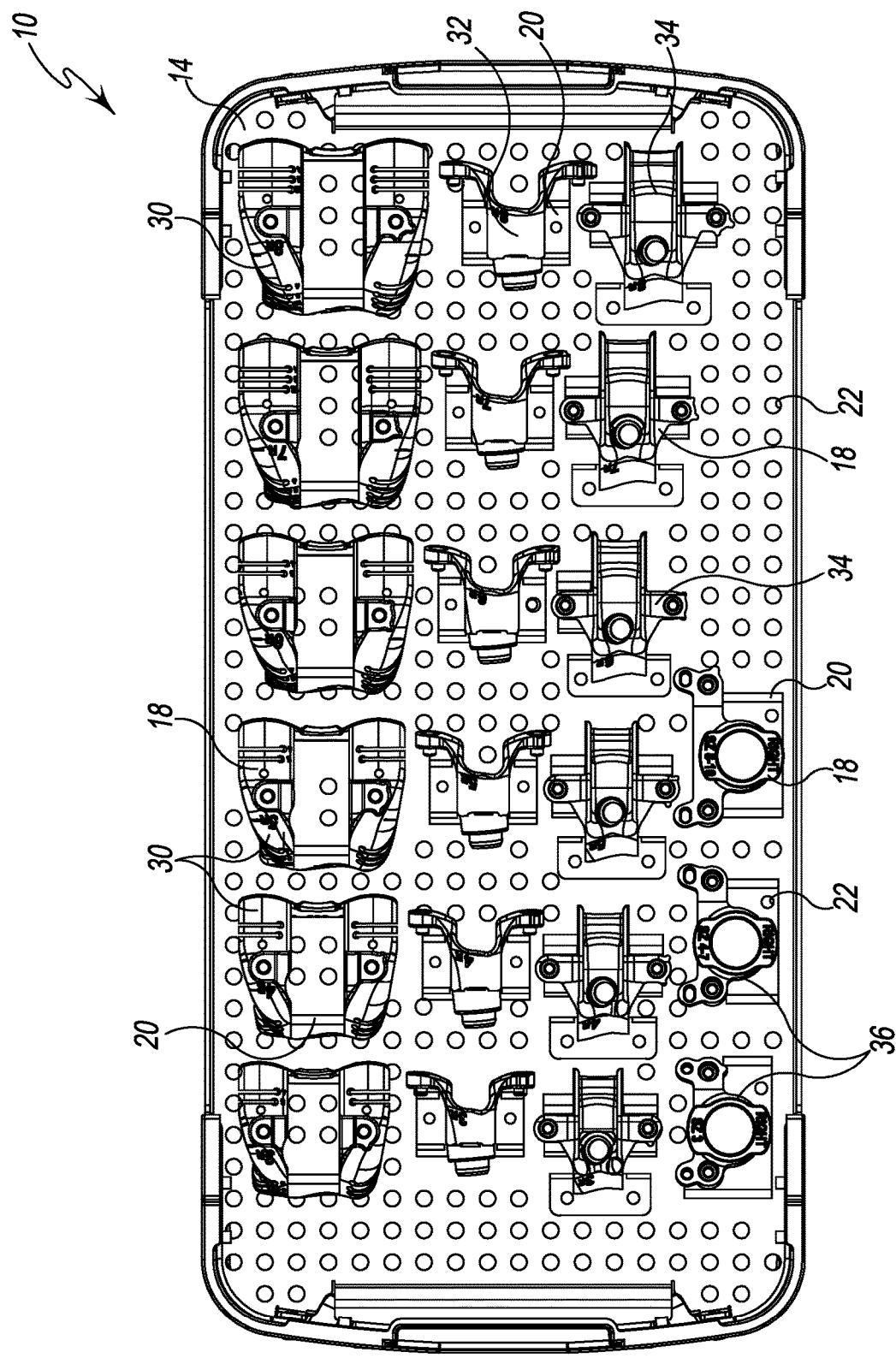
FIG. 1 is an elevation view of an exemplary embodiment of a right-limb side-specific orthopaedic surgical instrument assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
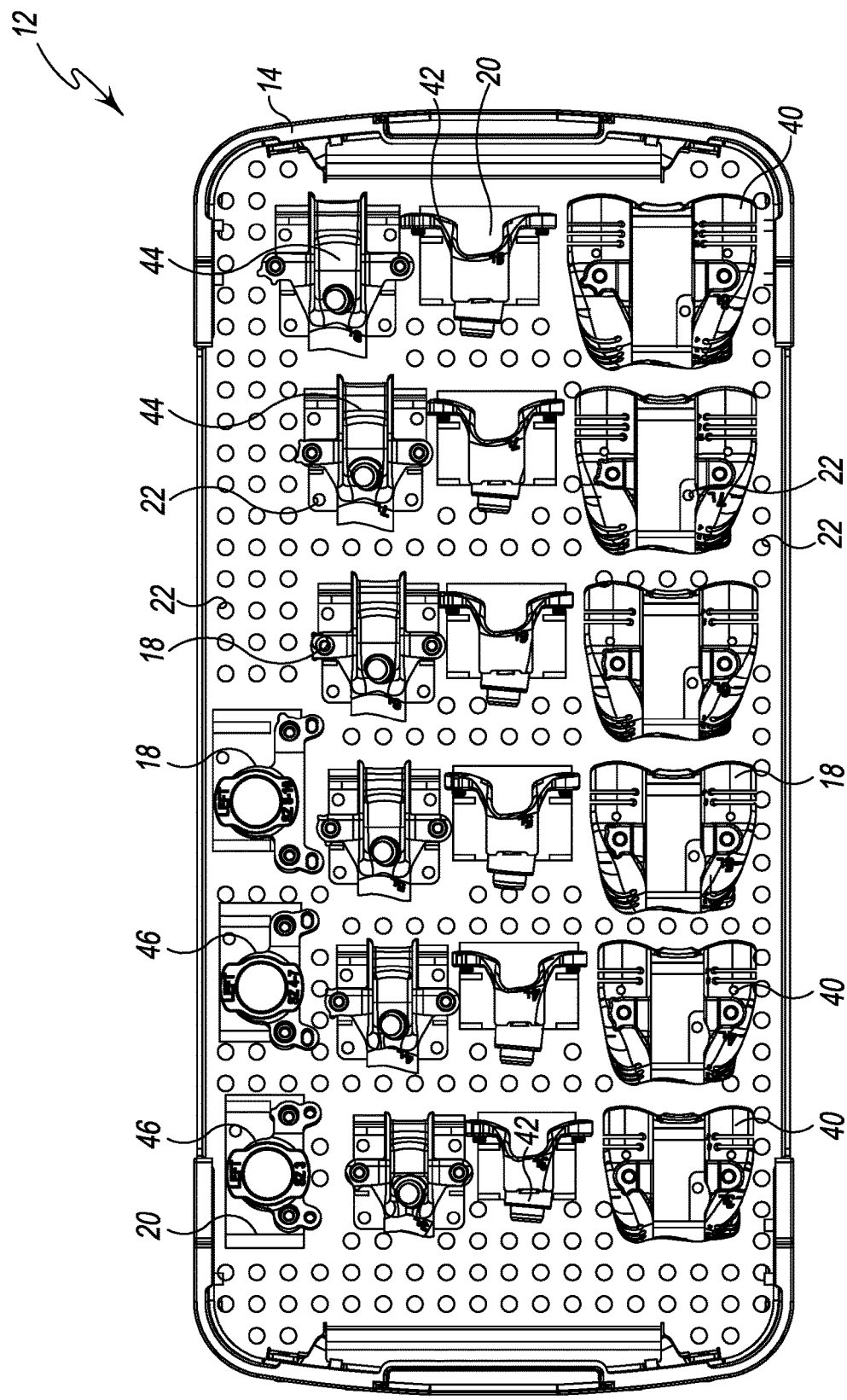
FIG. 2 is a view similar to FIG. 1, but showing a left-limb side-specific orthopaedic surgical instrument assembly.

Referring now to FIGS. 1 and 2, a pair of orthopaedic surgical instrument assemblies 10, 12 is shown. Each of the surgical instrument assemblies 10, 12 includes a sterilization tray 14 with a number of orthopaedic surgical instruments 18 positioned therein. What is meant herein by the term "orthopaedic surgical instrument" or "orthopaedic surgical instrument assembly" is a surgical tool for use by a surgeon in performing an orthopaedic surgical procedure. As such, it should be appreciated that, as used herein, the terms "orthopaedic surgical instrument" and "orthopaedic surgical instrument assembly" are distinct from orthopaedic implants or prostheses that are surgically implanted in the body of the patient.

In the exemplary embodiment described herein, each of the orthopaedic surgical instruments 18 of the instrument assemblies 10, 12 is a side-specific orthopaedic surgical instrument or a side-specific orthopaedic trial component. What is meant herein by the term "side-specific orthopaedic surgical instrument" or "side-specific orthopaedic trial component" is an orthopaedic surgical instrument or orthopaedic trial component that is designed specifically for use on one limb of a patient (i.e., a right or left), but not the other limb. For example, a right-limb side-specific femoral trial component is designed specifically for use on a patient's right femur, but not the patient's left femur. The opposite is the case for a left-limb side-specific femoral trial component—i.e., it is designed specifically for use on a patient's left femur, but not the patient's right femur. It should be appreciated that many orthopaedic surgical instruments, such as saw blades, drivers, stem trial components, tibial trial components, are not side-specific. Such non-side-specific instruments are designed to be used on both limbs of the patient (e.g., both the left and right femur). As such, what is meant herein by the term "non-side-specific instrument" is an orthopaedic surgical instrument that is designed to be used on both limbs of the patient.

The instrument sterilization trays 14 have a number of instrument retainers 20. The instrument retainers 20 are configured to retain the various differently-shaped orthopaedic surgical instruments 18 during sterilization, transport, and storage of the surgical instrument assemblies 10, 12. The instrument retainers 20 may be configured as brackets, connectors, cradles, or any other type of mechanism to retain the orthopaedic surgical instruments 18 in a desired location and orientation. It should be appreciated that the instrument retainers 20 could also take the form of specifically-shaped recesses or cavities formed in the instrument sterilization tray 14 into which the orthopaedic surgical instruments 18 could be inserted and retained. As can be seen in both FIGS. 1 and 2, some of the walls of the instrument sterilization tray 14 and some of the instrument retainers 20 have fluid holes 22 formed therein. The fluid holes 22 allow for the passage of sterilization fluid within the instrument sterilization tray 14 during the sterilization process.

The surgical instrument assemblies 10, 12 are side-specifically kitted. In particular, the surgical instrument assembly 10 includes various sizes of right-limb side-specific orthopaedic surgical instruments, but no left-limb side-specific orthopaedic surgical instruments. Oppositely, the surgical instrument assembly 12 includes various sizes of left-limb side-specific orthopaedic surgical instruments, but no right-limb side-specific orthopaedic surgical instruments.

Turning first to the surgical instrument assembly 10, it includes a plurality of right-limb side-specific femoral trial components 30. In the illustrative embodiment described herein, the femoral trial components 30 are embodied as cut-through femoral trial components; however, it should be appreciated that other types of femoral trial components are also contemplated for use. The right-limb side-specific femoral trial components 30 of the surgical instrument assembly 10 may be provided in a number of varying sizes to mimic the various sizes of the corresponding structures of the femoral implant (not shown) to be installed on the patient's distal femur. In one illustrative embodiment, the right-limb side-specific femoral trial components 30 of the surgical instrument assembly 10 may be provided in five different sizes—size 3, size 4, size 5, size 6, size 7, and size 8.

The surgical instrument assembly 10, also includes a plurality of right-limb side-specific intramedullary (IM) connector components 32. Like the femoral trial components 30, the right-limb side-specific IM connector components 32 of the surgical instrument assembly 10 may be provided in a number of varying sizes to mimic the various sizes of the corresponding structures of the femoral implant (not shown) to be installed on the patient's distal femur. In one illustrative embodiment, the right-limb side-specific IM connector components 32 of the surgical instrument assembly 10 may be provided in five different sizes—size 3, size 4, size 5, size 6, size 7, and size 8.

The surgical instrument assembly 10, further includes a plurality of right-limb side-specific box trial components 34. Like the other components 30, 32, the right-limb side-specific box trial components 34 of the surgical instrument assembly 10 may be provided in a number of varying sizes to mimic the various sizes of the corresponding structures of the femoral implant (not shown) to be installed on the patient's distal femur. In one illustrative embodiment, the right-limb side-specific box trial components 34 of the surgical instrument assembly 10 may be provided in five different sizes—size 3, size 4, size 5, size 6, size 7, and size 8.

In addition, the surgical instrument assembly 10 includes a plurality of right-limb side-specific femoral reamer guide components 36. The right-limb side-specific femoral reamer guide components 36 of the surgical instrument assembly 10 may be provided in a number of varying sizes to facilitate reaming of the patient's femur during installation of the femoral implant (not shown). In one illustrative embodiment, the right-limb side-specific femoral reamer guide components 36 of the surgical instrument assembly 10 may be provided in three different sizes—size 3, size 4-7, and size 8-10.

The surgical instrument assembly 12 is similar to as described above in regard to the surgical instrument assembly 10 except that its orthopaedic surgical instruments are left-limb side-specific instruments. Namely, the surgical instrument assembly 12 includes a plurality of left-limb side-specific femoral trial components 40. Like the femoral trial components 30, the femoral trial components 40 are embodied as cut-through femoral trial components; however, it should be appreciated that other types of femoral trial components are also contemplate for use. Similarly to as described above, the left-limb side-specific femoral trial components 40 of the surgical instrument assembly 10 may be provided in a number of varying sizes such as, for example, size 3, size 4, size 5, size 6, size 7, and size 8.

The surgical instrument assembly 12, also includes a plurality of left-limb side-specific intramedullary (IM) connector components 42. Like the IM connector components 32, the left-limb side-specific IM connector components 42 of the surgical instrument assembly 12 may be provided in a number of varying sizes such as, for example, size 3, size 4, size 5, size 6, size 7, and size 8. Similarly, the surgical instrument assembly 12, also includes a plurality of left-limb side-specific box trial components 44. The left-limb side-specific box trial components 44 of the surgical instrument assembly 12 may be provided in a number of varying sizes such as, for example, size 3, size 4, size 5, size 6, size 7, and size 8. And finally, in the illustrative embodiment described herein, the surgical instrument assembly 12 includes a plurality of left-limb side-specific femoral reamer guide components 46. Like their right-limb counterparts, the left-limb side-specific femoral reamer guide components 36 may be illustratively provided in three different sizes—size 3, size 4-7, and size 8-10.

As described above, the orthopaedic surgical instrument assemblies 10, 12 are configured as side-specific systems, as opposed to size-specific systems. In particular, when fully kitted and prepared for use in a surgical procedure, the orthopaedic surgical instrument assembly 10 is configured for use on a right-limb of a patient and is, therefore, devoid of any left-limb side-specific orthopaedic surgical instruments. In other words, when the instrument sterilization tray 14 of the surgical instrument assembly 10 is fully loaded—i.e., each of the instrument retainers 20 has an instrument retained therein, none of the retainers 20 includes left-limb side-specific surgical instruments. In the illustrative embodiment described herein, a right-limb side-specific orthopaedic surgical instrument is positioned in each of the instrument retainers 20 of the instrument sterilization tray 14 of the surgical instrument assembly 10 when the tray is fully loaded; however, it should be appreciated that in some embodiments, non-side-specific orthopaedic surgical instruments may be placed in the instrument sterilization tray 14 of the surgical instrument assembly 10 along with the right-limb side-specific surgical instruments.

Oppositely, when fully kitted and prepared for use in a surgical procedure, the orthopaedic surgical instrument assembly 12 is configured for use on a left-limb of a patient and is, therefore, devoid of any right-limb side-specific orthopaedic surgical instruments. Specifically, when the instrument sterilization tray 14 of the surgical instrument assembly 12 is fully loaded—i.e., each of the instrument retainers 20 has an instrument retained therein, none of the retainers 20 includes right-limb side-specific surgical instruments. In the illustrative embodiment described herein, a left-limb side-specific orthopaedic surgical instrument is positioned in each of the instrument retainers 20 of the instrument sterilization tray 14 of the surgical instrument assembly 12 when the tray is fully loaded; however, it should be appreciated that in some embodiments, non-side-specific orthopaedic surgical instruments may be placed in the instrument sterilization tray 14 of the surgical instrument assembly 10 along with the left-limb side-specific surgical instruments.

In use, the orthopaedic surgical instrument assembly 10 is used during orthopaedic surgical procedures on a right-limb of a patient, with the orthopaedic surgical instrument assembly 12 being used during orthopaedic surgical procedures on a left-limb of a patient. The instrument sterilization trays 14 of the respective instrument systems 10, 12 are first populated with the corresponding side-specific orthopaedic surgical instruments. Namely, right-limb side-specific orthopaedic surgical instruments are positioned in the instrument sterilization tray 14 of the surgical instrument assembly 10 and left-limb side-specific orthopaedic surgical instruments are positioned in the instrument sterilization tray 14 of the surgical instrument assembly 12. In the case of the illustrative embodiment described herein, the right-limb side-specific femoral trial components 30, the right-limb side-specific IM connector components 32, the right-limb side-specific box trial components 34, and the right-limb side-specific femoral reamer guide components 36 are positioned in the retainers 20 of the instrument sterilization tray 14 of the surgical instrument assembly 10, with the left-limb side-specific femoral trial components 40, the left-limb side-specific IM connector components 42, the left-limb side-specific box trial components 44, and the left-limb side-specific femoral reamer guide components 46 being positioned in the retainers 20 of the instrument sterilization tray 14 of the surgical instrument assembly 12. In such a way, the instrument sterilization tray 14 of the surgical instrument assembly 10 is devoid of left-limb side-specific surgical instruments and the instrument sterilization tray 14 of the surgical instrument assembly 12 is devoid of right-limb side-specific instruments. However, in some embodiments, non-side-specific instruments may be placed in the sterilization tray 14 of either instrument assembly 10, 12.

Once the sterilization trays 14 have been filled in such a manner, the instrument assemblies 10, 12 are sterilized. Depending on whether the orthopaedic procedure being performed is a right-limb procedure or a left-limb procedure (e.g., a right knee procedure or a left knee procedure), the corresponding sterilized instrument assembly 10, 12 is then delivered to the operating room and utilized by the surgical staff during performance of the procedure.

Kitting the instrument assemblies 10, 12 in the manner described herein reduces the amount of unused instruments in the operating room since instruments for the opposite limb (i.e., the limb not being operated on) are not present. The weight of the fully-loaded trays 14 can also be reduced by not including such unneeded instruments. Moreover, by not including the unneeded instruments, post-operative cleaning and sterilization is also improved since the number of unused instruments may be reduced.

The systems and methods described herein may find particular advantages in the performance of procedures such as revision knee procedures. However, many of those advantages may also be recognized in instruments used in the performance of other orthopaedic knee procedures, along with procedures for other joint replacements (e.g., hip-, shoulder-, or ankle-replacement procedures).

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of using a surgical instrument system, comprising:
   positioning (i) a plurality of right-limb side-specific orthopaedic trial components, each of which having a size that is different from the size of at least some of the other of the plurality of right-limb side-specific orthopaedic trial components, in a first instrument sterilization tray and (ii) a plurality of left-limb side-specific orthopaedic trial components, each of which having a size that is different from the size of at least some of the other of the plurality of left-limb side-specific orthopaedic trial components, in a second instrument sterilization tray such that (a) the first instrument sterilization tray is devoid of any of the plurality of left-limb side-specific orthopaedic trial components, and (b) the second instrument sterilization tray is devoid of any of the plurality of right-limb side-specific orthopaedic trial components,
   sterilizing the first instrument tray and the second instrument tray, and
   utilizing at least one of the first instrument tray and the second instrument tray during performance of an orthopaedic surgical procedure.

2. The method of claim 1, wherein utilizing at least one of the first instrument tray and the second instrument tray comprises utilizing the first instrument tray during performance of an orthopaedic surgical procedure on a right limb of a patient.

3. The method of claim 1, wherein utilizing at least one of the first instrument tray and the second instrument tray comprises utilizing the second instrument tray during performance of an orthopaedic surgical procedure on a left limb of a patient.

4. The method of claim 1, wherein positioning the plurality of right-limb side-specific orthopaedic trial components in the first instrument sterilization tray and the plurality of left-limb side-specific orthopaedic trial components in the second instrument sterilization tray comprises:
   positioning a plurality of right-limb side-specific femoral trial components in the first tray, and
   positioning a plurality of left-limb side-specific femoral trial components in the second tray.

5. The method of claim 1, wherein positioning the plurality of right-limb side-specific orthopaedic trial components in the first instrument sterilization tray and the plurality of left-limb side-specific orthopaedic trial components in the second instrument sterilization tray comprises:
   positioning a plurality of right-limb side-specific intramedullary connector components in the first tray, and
   positioning a plurality of left-limb side-specific intramedullary connector components in the second tray.

6. The method of claim 1, wherein positioning the plurality of right-limb side-specific orthopaedic trial components in the first instrument sterilization tray and the plurality of left-limb side-specific orthopaedic trial components in the second instrument sterilization tray comprises:
   positioning a plurality of right-limb side-specific box trial components in the first tray, and
   positioning a plurality of left-limb side-specific box trial components in the second tray.

7. The method of claim 1, wherein positioning the plurality of right-limb side-specific orthopaedic trial components in the first instrument sterilization tray and the plurality of left-limb side-specific orthopaedic trial components in the second instrument sterilization tray comprises:
   positioning a plurality of right-limb side-specific femoral reamer guide components in the first tray, and
   positioning a plurality of left-limb side-specific femoral reamer guide components in the second tray.

\* \* \* \* \*